United States Patent [19]
Lattner et al.

[11] Patent Number: 6,093,865
[45] Date of Patent: Jul. 25, 2000

[54] PRODUCTION OF ALKENYL BRIDGED RING COMPOUNDS

[75] Inventors: James R. Lattner, Seabrook; Leonel E. Sanchez, League City, both of Tex.; Christopher L. Becker, Russell, Kans.; Bruce C. Devoy, Baton Rouge, La.

[73] Assignee: Exxon Chemical Patent Inc., Houston, Tex.

[21] Appl. No.: 09/098,237

[22] Filed: Jun. 16, 1998

Related U.S. Application Data

[63] Continuation-in-part of application No. 08/818,519, Mar. 14, 1997, abandoned, which is a continuation-in-part of application No. 08/366,709, Dec. 30, 1994, abandoned, which is a continuation-in-part of application No. 08/175,443, Dec. 30, 1993, Pat. No. 5,569,804.

[51] Int. Cl.[7] .................................. C07C 2/50; C07C 7/00
[52] U.S. Cl. ........................ 585/361; 585/354; 585/362; 585/361; 585/366; 585/800; 585/905
[58] Field of Search ..................................... 585/905, 354, 585/361, 362, 366, 800

[56] References Cited

U.S. PATENT DOCUMENTS

| | | |
|---|---|---|
| 3,590,089 | 6/1971 | Robota . |
| 3,728,406 | 4/1973 | Vrinssen et al. . |
| 3,922,317 | 11/1975 | Jhawar . |
| 5,569,804 | 10/1996 | Lattner et al. . |

FOREIGN PATENT DOCUMENTS

| | | |
|---|---|---|
| 2242351 | 3/1975 | France . |
| WO 95/18087 | 7/1995 | WIPO . |

*Primary Examiner*—Elizabeth D. Wood
*Attorney, Agent, or Firm*—Bradley A Keller; Linda K. Russell

[57] ABSTRACT

The present invention relates to a method for using a single distillation column to recover the reactants and products from the reaction of a cyclic diolefin and an olefin to produce an alkenyl bridged ring compound.

17 Claims, 4 Drawing Sheets

PRODUCTION OF ALKENYL BRIDGED RING COMPOUNDS

This patent application is a continuation-in-part of U.S. patent application Ser. No. 08/818,519 filed Mar. 14, 1997, now abandoned, which is a continuation-in-part of U.S. patent application Ser. No. 08/366,709 filed Dec. 30, 1994, now abandoned, which is a continuation-in-part of U.S. patent application Ser. No. 08/175,443 filed Dec. 30, 1993, now U.S. Pat. No. 5,569,804.

FIELD OF THE INVENTION

The present invention relates to an improved process for recovering alkenyl bridged ring compounds produced by reacting olefins with cyclic diolefins and for recovering and using the unreacted cyclic diolefins to produce additional amounts of the alkenyl bridged ring compounds.

BACKGROUND OF THE INVENTION

One way to produce an alkenyl bridged ring compound is to use a Diels-Alder reaction, which is the additive reaction of an olefin with a cyclic diolefin. For example, 5-vinyl-2-norbornene (an alkenyl bridged ring compound) may be produced by the Diels-Alder reaction of 1,3 butadiene (an olefin) with 1,3-cyclopentadiene (a cyclic diolefin). 5-vinyl-2-norbornene (VNB) is very desirable as it is an intermediate in the production of 5-ethylidene-2-norbornene (ENB), a termonomer used in the production of ethylene-propylene-diene monomer (EPDM) rubbers.

The conditions necessary to bring about the Diels-Alder reaction of 1,3-butadiene (BD) with 1,3-cyclopentadiene (CPD) are well known in the art. In particular, BD may be contacted with CPD in the liquid phase at temperatures of from 100° to 200° C. and a pressure of from 150 to 300 psi (1,034–2,068 kPa). It is not necessary to use a catalyst to advance the Diels-Alder reaction. The reaction is generally completed in 0.1 to 100 hours and is usually conducted under an inert atmosphere. Preferably, the reaction may be conducted in a liquid state, most preferably in a liquid-full reaction vessel.

When making VNB the preferred reaction occurs between BD and CPD, however, undesirable polymerization reactions may also occur. For example, BD monomers may react with each other to form polymers. Similar polymerization reactions may occur between CPD monomers. Undesirable by-products include dimerization of BD to form 4:vinyl-1-cyclohexene (VCH), rearrangement of VNB to form 4, 7, 8, 9-tetrahydroindene (THI) and Diels-Alder adducts of BD or CPD with VNB, VCH, or THI (hereinafter referred to as "trimers of BD/CPD").

CPD will readily react with itself to form dicyclopentadiene (DCPD). In turn, DCPD will crack upon heating, back to the CPD monomer. Therefore, both CPD and/or DCPD can be used as the cyclic diolefin feedstock in the production of alkenyl bridged ring compounds. As used herein, the term "(di)cyclopentadiene" refers to cyclopentadiene, dicyclopentadiene or mixtures thereof in the reaction mixture. In the present application, cyclopentadiene and dicyclopentadiene are regarded as the same substance in the calculation of the conversion of raw materials and, hence, the transformation of cyclopentadiene into dicyclopentadiene, and vice versa is not considered a conversion.

Certain compounds are known which suppress or inhibit the undesired polymerization reactions. Any one or combination of these inhibitor compounds may be added to the reactants in order to produce more VNB from the same amount of starting material and to avoid plugging certain parts of the reaction apparatus with the high molecular weight polymers which might otherwise be formed. Many inhibitor compounds are known in the art including 2,6-di-t-butyl-p-cresol, diphenylinitrosamine, and N-substituted p-phenylenediamines.

In addition to the problems caused by fouling, the undesired byproducts are difficult to separate from VNB which create additional problems in the production process of making VNB.

As taught by U.S. Pat. No. 3,728,406, improved selectivity during the production of VNB, or any alkenyl bridged ring compounds, can be achieved by two methods. First, the starting material may be limited to the CPD monomer, rather than the DCPD dimer. This results in higher conversion of the (di)cyclopentadiene to VNB. Second, the reaction can be discontinued early after only a relatively small portion of the total CPD and/or DCPD has been consumed. One of the disadvantages of this process is that a substantial amount of residual DCPD is left in the reactor effluent. However, this residual DCPD can be recovered to produce additional alkenyl bridged ring compound. Steps to recover the DCPD include: (1) vacuum distillation to separate the DCPD from the THI and trimers of BD/CPD, or (2) selectively cracking the DCPD to CPD, which is then easily separated from the THI and trimers of BD/CPD because it is much more volatile. Unfortunately, either method requires additional processing equipment and the conditions used to crack DCPD typically result in fouling of the equipment.

Thus, a need exists in the art for a simple and economical method to recover the residual dimer of the cyclic diolefin from the production of an alkenyl bridged ring compound, by cracking the dimer to cyclic diolefin monomer, and recycling the monomer to produce more of the desired alkenyl bridged ring compound without fouling of the equipment.

SUMMARY OF THE INVENTION

The present invention relates to a continuous process which utilizes a single process step to recover the reactants and products from the Diels-Alder reaction of a cyclic diolefin and an olefin to produce an alkenyl bridged ring compound. The single process step utilizes a distillation column, to which the reaction effluent is fed. The unreacted cyclic diolefin and olefin are removed from the column as overhead products and recycled to the reaction feed mixture to produce additional alkenyl bridged ring compound. The alkenyl bridged ring compound is removed as a side stream at a location above the feed to the column, which can then be purified further by conventional means. The higher boiling reaction byproducts and dimer of the cyclic diolefin are treated in the bottom of the column, such that the dimer of the cyclic diolefin is selectively "cracked", or converted back to the monomer, which then travels to the top of the column and is recovered with the recycle stream to the reaction feed mixture.

Features of this invention are that the desired alkenyl bridged ring compound is separated from both the monomer and dimer of the unconverted cyclic diolefin feed, while at the same time the dimer of the cyclic diolefin is separated from the heavy reaction by-products by conversion to the cyclic diolefin monomer. The cyclic diolefin monomer from both the reaction effluent, as well as that converted from the dimer, are simultaneously recovered in the present invention for recycle to the reaction feed mixture. Additional alkenyl bridged ring compound can then be produced from this recovered cyclic diolefin monomer.

In another embodiment of the present invention, norbornene (NB) or substituted norbornenes are produced in high yields by first reacting a monoolefin with a cyclic diolefin in a Diels-Alder reaction. The heavy byproducts from the Diels-Alder reaction are decomposed under conditions effective to produce a material which comprises at least NB or one of the starting materials—the mono-olefin or the cyclic diolefin. Norbornene can then be polymerized or co-polymerized with another olefin such as ethylene to form polymers. The polymers and copolymers have useful physical, chemical and/or optical properties, which render them useful in making CD-ROM disks, adhesives, and other products.

These advantages and other advantages of the present invention can be better understood from the following detailed description, the attached drawings and the appended claims.

DETAILED DESCRIPTION OF THE INVENTION

Although the foregoing and following description often refers to the separation of reactants and products from the production of VNB, the invention is not limited to such use. The present invention may be used for producing any alkenyl bridged ring compound made from a Diels-Alder reaction of a cyclic diolefin, such as CPD and/or DCPD or methyl cyclopentadiene and/or di-methyl-cyclopentadiene, with an olefin, such as ethylene, acetylene, propylene, 1,3-butadiene, 1,2-butadiene, piperylene, isoprene, etc.

Figure 1:
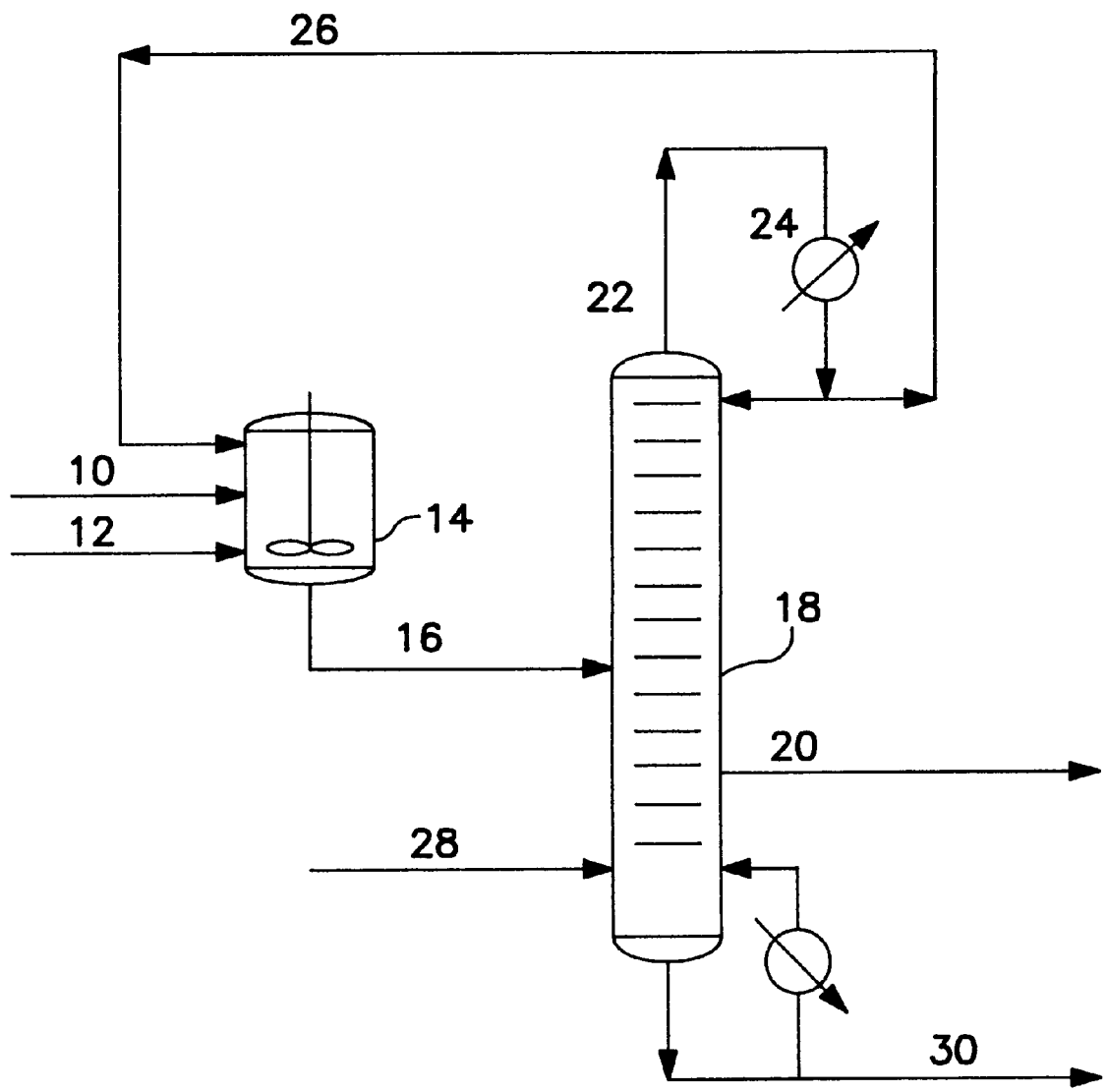
FIG. 1 is a schematic diagram which illustrates the equipment and the flow of a process according to one embodiment of the present invention.

Referring now to FIG. 1, in order to produce VNB, BD and (di)cyclopentadiene are fed via a line 10 and a line 12, respectively, into a Diels-Alder reactor 14 and reacted using known methods. Preferably, the reaction is stopped when about 50 percent of the (di)cyclopentadiene feed has been converted, as described in U.S. Pat. No. 3,728,406. As noted in U.S. Pat. No. 3,728,406, the reaction time required to reach the desired degree of conversion of 50 percent or lower of the (di)cyclopentadiene will vary according to reaction conditions, such as temperature, pressure, ratio of reactants, presence and amount of catalyst, if any, etc. Thus, no absolute reaction times can be set forth. However, one skilled in the art can easily determine the necessary reaction time by performing an orienting experiment using a given set of reaction conditions. Generally, reaction times should be less than one hour but greater than ten minutes.

Once the reaction has reached the desired conversion level, the effluent from the Diels-Alder reactor may be fed via a line 16 to a distillation column 18. The effluent should contain BD, CPD, diluent (typically a C6-C7 aliphatic or aromatic solvent), VCH, VNB, THI, DCPD, and trimers of BD and CPD.

The distillation column 18 should be maintained at an operating pressure of between about 5–30 psia (34.4–206.8 kPa), preferably between about 11–17 psia (75.8–117.2 kPa). Higher pressures result in unacceptable levels of conversion of VNB to THI and an increased potential to foul the column reboiler. Lower pressures would result in column temperatures which would be insufficient to achieve significant cracking of DCPD to CPD. The temperature in the bottom of the column should be maintained at least above about 130° C. (266° F.), preferably between about 170–190° C. (338–374° F.), and more preferably about 175° C. (347° F.).

The crude VNB, which also includes some VCH, THI, and DCPD, is removed from the column, preferably in a side stream via a line 20, which should be located at a point below the feed. The removal of VNB as a side stream, rather than leaving the VNB in the bottoms, minimizes the undesired conversion of VNB to THI. The VNB side stream subsequently is treated with additional distillation steps (not shown), using known procedures, to remove the lighter boiling VCH and the heavier-boiling THI and DCPD.

Under the foregoing column conditions, the lighter boiling BD and CPD from the effluent travels up the distillation column 18, along with the light boiling diluent, and may be removed as overhead via a line 22 and recycled to the Diels-Alder reactor 14, e.g., via a heat exchanger 24 and a recycling line 26.

The remaining bottoms should contain primarily THI, DCPD, and trimers of BD/CPD and other oligimers of CPD, BD, and acyclics. The bottoms may be left in the distillation column, or otherwise exposed to the foregoing column conditions, for at least fifteen minutes, preferably at least one hour, during which time approximately 90% of the DCPD in the bottoms will crack to monomeric CPD. The resulting CPD will travel up the column and may be removed as overhead via line 22 and recycled to produce additional VNB.

The resulting DCPD-depleted heavy product may be removed as bottoms via line 30.

One surprising result when the bottoms is left in the column 18 for at least fifteen minutes to crack the residual DCPD is the very low polymer formation or fouling of the equipment. The literature teaches that, when trying to crack DCPD to CPD in the liquid phase, it is essential to use a high-boiling inert solvent to minimize the formation of CPD oligomers which foul the equipment. See, e.g., U.S. Pat. No. 3,590,089, which is incorporated in its entirety herein by reference. No such solvent is added to the bottoms during cracking according to the present invention. Therefore, without limiting the invention to any particular theory, it appears that the THI and trimers of BD/CPD in the bottoms behave as diluents in the cracking reaction. This result is unexpected since these trimers are not inert to additional thermal Diels-Alder reactions. Nevertheless, analysis of the reboiler heat transfer coefficient during extended runs show that the coefficient holds fairly stable. Visual inspection of the reboiler following the total period of the run showed only a very thin film of polymer on the heat transfer surfaces. No polymer collected on the filters in the bottoms product effluent line.

Another surprising result when the bottoms is cracked is the very high DCPD cracking level achieved (approximately 90%) in the boiling liquid of the column bottoms at atmospheric pressure and at a temperature as low as 175° C. (347° F.). Again, without limiting the present invention to any particular theory, it appears that the presence of high-boiling trimers of BD/CPD in the bottoms is necessary to achieve the desired cracking levels without the external addition of a high boiling solvent.

The "in column" cracking of DCPD in the present invention can result in two additional benefits. First, the fresh make-up DCPD may be passed through the distillation column 18, e.g., via line 28, before being fed to the Diels-Alder reactor 14. This allows virtually all of the (di) cyclopentadiene feed to the Diels-Alder reactor 14 to be monomeric CPD, rather than a mixture of CPD and DCPD. Second, when further purification of the crude VNB takes place, the portion of the VNB side stream containing DCPD can be returned to the bottoms in the distillation column 18 for cracking according to the present invention.

Figure 2:
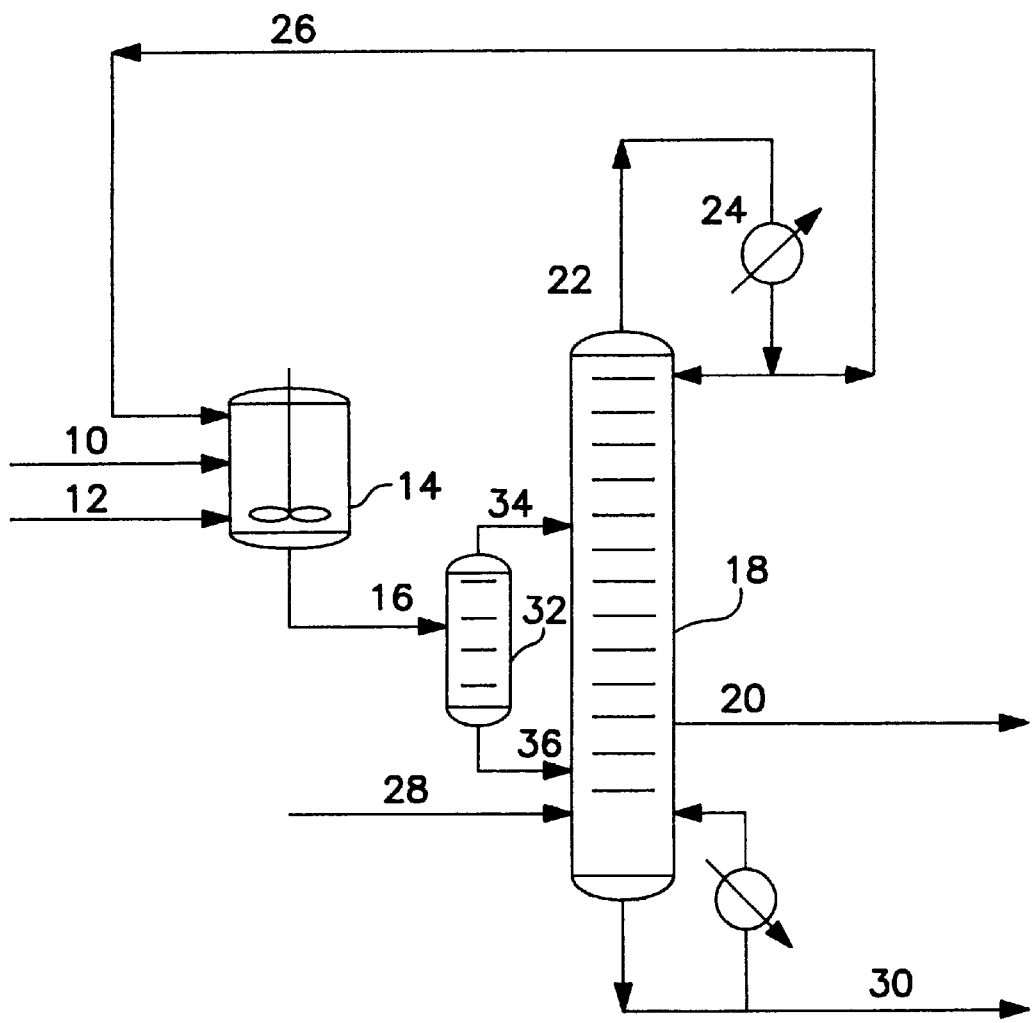
FIG. 2 is a schematic diagram which illustrates the equipment and the flow of a process according to another embodiment of the present invention.

With reference to FIG. 2, another embodiment of the present invention is illustrated. This embodiment includes an improvement that substantially reduces the loss of other materials with the VNB sidestream. This is done by performing a crude separation of the Diels-Alder reaction effluent 16 prior to feeding it to the recycle distillation column 18. A small column 32, referred to as a "flash column," is used to separate the light-boiling effluent from the dimer. This separation flows easily because of the wide difference in boiling points (in the case of toluene as diluent and the DPCD as the dimer, the boiling point difference is about 60° C.). An overhead stream 34, which is substantially free of dimer, is fed from the flash column 32 to the distillation column 18 at a location above the sidestream draw 20. The bottoms 36, which is substantially free of the diluent and lighter boiling materials, is fed from the flash column 32 at a location below the sidestream draw 20. The Diels-Alder reaction product, such as VNB, boils between the diluent and the dimer, and will exit both the top and bottom of the flash column 32, which is not problematic. The recycle distillation column 18 can now produce a Diels-Alder sidestream product that contains all of the desired Diels-Alder reaction product, such as VNB, but is free of both the dimer and the diluent, substantially reducing the losses of either material which would be unavoidable if practiced without the benefit of the flash column 32.

In this embodiment, the flash column 32 may be operated in a conventional manner, using a reboiler and a condenser. Rather than using a conventional boiler as heat source for the flash column 32, some of the bottoms from the recycle column 18 may be fed to the bottoms of the flash column 32 by direct contact heat exchange. In addition, the condenser may be eliminated by utilizing a small portion of the liquid distillate from the recycle column 18 as reflux for the flash column 32.

Figure 4:
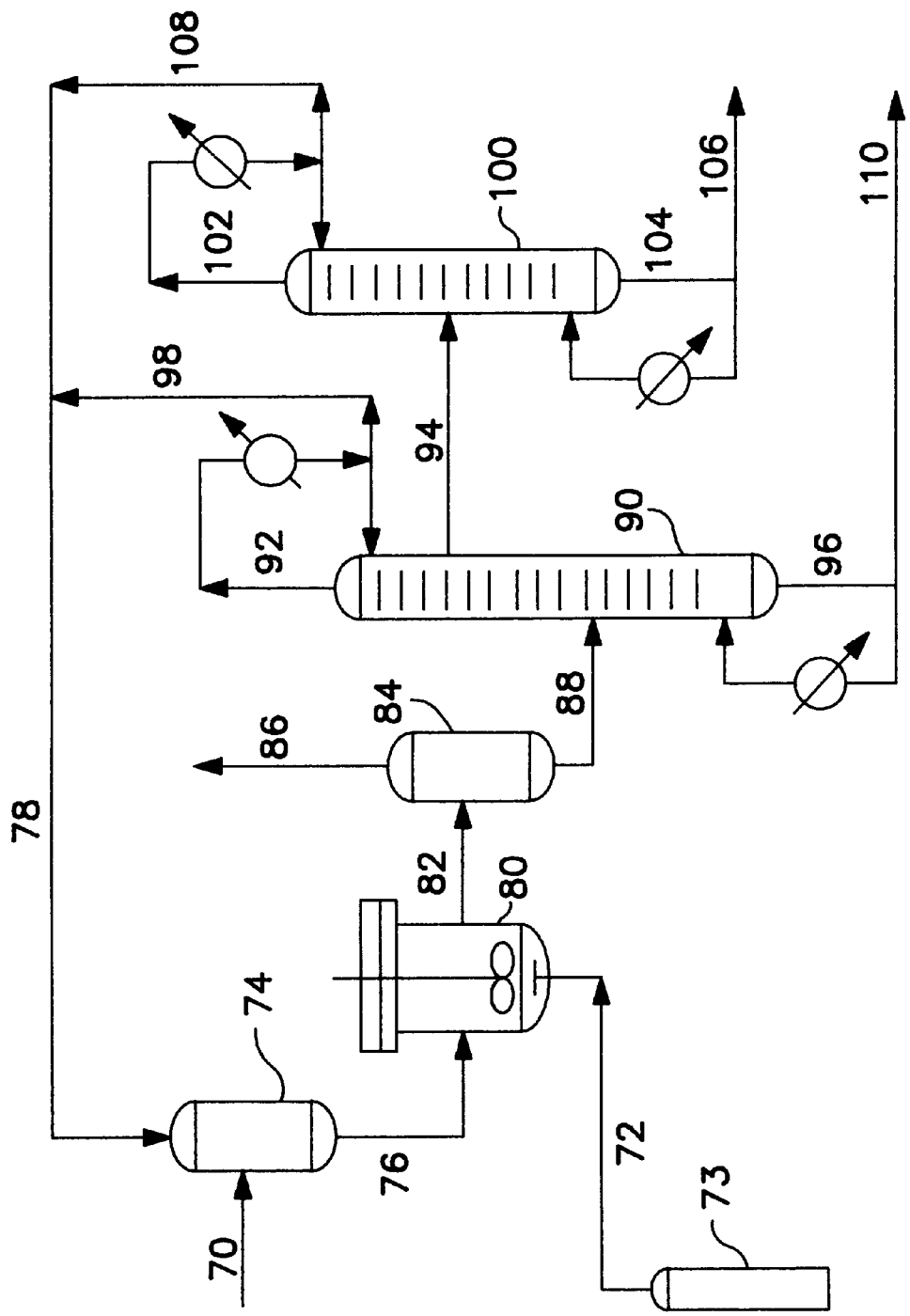
FIG. 4 is a schematic diagram which illustrates the equipment and the flow of a process according to yet another embodiment of the present invention.

As shown in FIG. 4, another embodiment of the present invention is used to produce norbornene or substituted norbornenes as the desired alkenyl bridged ring products. The Diels-Alder reaction is carried out between a mono-olefin and a cyclic diolefin as starting materials. The Diels-Alder reaction can be a thermal reaction or a catalyzed reaction. Suitable catalysts for the Diels-Alder reaction are known in the art.

Mono-olefins useful as starting materials include, but are not, and necessarily limited to ethylene, propylene, butene-1, cis-butene-2, transbutene-2, isobutylene, cyclopentene, vinyl chloride, vinyl acetate, allyl acetate, styrene, p-methylstyrene, and mixtures thereof.

Cyclic diolefins useful as starting materials include, but are not necessarily limited to cyclopentadiene, methylcyclopentadiene, other substituted cyclopentadienes, 1,3-hexadiene, substituted 1,3-hexadienes, and mixtures thereof. Dimers and mixed dimers of cyclopentadienes also can be used, including, but not necessarily limited to dicyclopentadiene, dimethylcyclopentadiene, cyclopentadiene-methylcyclopentadiene codimer, and mixtures thereof.

As shown in FIG. 4, a mono-olefin feed 72 is introduced from a container 73 into the bottom of a Diels-Alder reactor 80 through a sparger or other type of distributor known in the art. A liquid feed 76 comprising cyclic diolefin is fed separately to the reactor 80 from a feed drum 74. The liquid feed 76 comprises a recycle cyclic diolefin stream 78 (described more fully below), and a liquid feed 70 comprising make-up cyclic diolefin and/or cyclic diolefin dimer, a light solvent and a heavy solvent as diluent.

The reactor 80 is equipped with a temperature control system to control the reaction temperature, and a back pressure regulator to control the reaction pressure. The reactor 80 also has a device for agitation and mixing. Agitation is a preferred way to make the reaction mixture uniform. Different reactor systems may be used, including, but not necessarily limited to batch, semi-continuous, and continuous systems. A continuous stirred-tank reactor system is preferred.

An effluent 82 from reactor 80 is flashed into a separator drum 84, where the bulk of the unreacted mono-olefin preferably is removed as a vapor fraction 86. A liquid fraction 88 from the separator drum 84, comprising crude norbornene product, unreacted starting materials, and heavy by-products, is sent to a recycle distillation column 90 which is operated near or at sub-atmospheric pressures. The cyclic diolefin monomer and the light solvent are distilled off as overhead 92 and recycled back to the Diels-Alder reactor 80 as part of a stream 98 via the liquid feed drum 74.

A crude norbornene product 94 is removed through a sidestream drawoff in the recycle distillation column 90 at a point above the liquid feed line of liquid fraction 88. The crude norbornene product 94 is sent to a second distillation column 100.

Heavy by-products, cyclic diolefin dimer, heavy solvent, and other heavy materials are distilled as a fraction 96 to the bottoms of the recycle distillation column 90. The fraction 96 is heated in the recycle distillation column 90 and subjected to conditions effective to decompose at least a portion of the heavy by-products into at least one of the starting materials—the mono-olefin, the cyclic diolefin, the dimer of the cyclic diolefin, the norbornene product, or mixtures thereof—and recycled back to the feed drum 74 via an overhead 92 and a stream 98. Very heavy materials and catalysts, if any are used for the Diels-Alder reaction, are discharged as a waste stream 110 and disposed.

The crude norbornene product 94 sent to the second distillation column 100 is purified by removing light materials as an overhead 102 which is recycled back to the feed drum 74. High purity norbornene is recovered as a bottoms stream 106.

The conversion of the cyclic diolefin and the cracking of the heavy by-products can be controlled, optimized, or maximized by selecting suitable combinations of the Diels-Alder reaction conditions, the monoolefin-to-cyclic diolefin ratios, the recycle conditions, and the amounts of recycles.

The reaction conditions of various parts of this embodiment depend on many factors—the starting mono-olefin and cyclic diolefin, the desired space-time yield, the desired overall yield of the product, the tolerance for heavy materials, the desired amount of recycle, and other factors.

For the Diels-Alder reactor 80, the operating temperature is in the range of from about 120° C. to about 230° C., preferably in the range of from about 175° C. to about 210° C. The operating pressure is in the range of from about 150 psia to about 6000 psia, preferably from about 400 psia to about 2000 psia. The residence time is in the range of from about 0.1 hours to about 3.0 hours, preferably from about 0.5 hours to about 2.0 hours.

Generally, the higher the operating temperature, the higher the reaction rate. Too high a temperature may cause formation of excess undesired products. Higher pressures tend to cause higher concentrations of the reactants in the liquid phase and improve reaction rates. Residence time is selected to reach a desired conversion level without producing undesired amounts of byproducts.

The operating pressure in the flash drum 84 is in the range of from about 0 psia to about 50 psia. The operating temperature in the flash drum 84 may be controlled by means known in the art to effect the desired separations.

The recycle distillation column 90 is operated at a pressure in the range of from about 1 psia to about 40 psia, preferably from 10 psia to about 25 psia. The bottoms of the recycle distillation column 90 is operated at a temperature in the range of from about 125° C. to about 270° C., preferably from about 180° C. to about 250° C.

The second distillation column 100 is operated at a temperature, pressure and other conditions effective to purify the particular norbornene product of the reaction. For the parent norbornene itself, the operating temperature is set in the range of from about 10° C. to about 150° C., preferably from about 35° C to about 110° C., and the operating pressure is in the range of from about 1 psia to about 50 psia.

When the Diels-Alder reaction is between ethylene and cyclopentadiene, the product is 2-norbornene (NB) and the major heavy by-product is octahydro-(1,4,5,8)-dimethanonaphthalene (also called tetracyclododecene, hereinafter referred to as TCD). The conversion of DCPD to CPD may be as high as in the range of from about 89% to about 93%. The conversion of the heavy by-product TCD to NB and CPD can be as high as in the range of from about 53% to about 64%.

Both the light solvent and the heavy solvent may act as diluents. A light solvent may be used in the absence of a heavy solvent. A heavy solvent may be used in the absence of a light solvent. If too little solvent is used, the desired effects cannot be achieved. If too much solvent is used, recycle of the solvent will become burdensome and costly. The amount of the solvent used also depends on the physical and chemical properties of the solvent, the particular alkenyl bridged ring product to be produced, the heavy byproducts present, and other reaction conditions.

The light solvent does not have to be a single-component material. Mixtures may be used. Suitable light solvents comprise hydrocarbons which do not react substantially with either the mono-olefin or the cyclic diolefin starting material and have a boiling point below the boiling point of the target norbornene. When norbornene is the desired product, the light solvent should have a boiling point below about 96° C. A light solvent, preferably hexane, is a preferred solvent for norbornene production. The amount of light solvent used in the present invention is in the range of from about 0 wt % to about 90 wt % of the liquid feed, preferably from about 20 wt % to about 40 wt %.

The heavy solvent does not have to be a single-component material. Mixtures may be used. Suitable heavy solvents comprise hydrocarbons which do not react substantially with either the mono-olefin or the cyclic diolefin starting material and have a boiling point above the temperature required to crack the heavy by-product to a desired conversion level—preferably a level of about 5wt % or higher.

When TCD is the heavy by-product formed in the production of norbornene, a heavy solvent having a boiling point of about 190° C. and higher will be effective to achieve about 50 wt % or higher conversions of TCD during cracking. Exxon's Aromatic 200® (b.p. range from about 217° C. to about 293° C.) is a heavy solvent suitable for converting TCD to NB and CPD. Another suitable solvent is Exxon's Exxsol D-110® (b.p. range from about 247° C. to about 267° C.). If conversion of less than 50 wt % of the TCD is desired, a lower boiling heavy solvent may be used. The amount of heavy solvent used in the present invention is in the range of from about 0 wt % to about 90 wt % of the liquid feed, preferably from about 5 wt % to about 15 wt %.

The following examples are presented for illustrative purposes only and not intended to limit the description in any manner.

EXAMPLE I

This process was demonstrated as described below in a continuous pilot unit for 6 weeks.

13.0 lb./hr BD and 13.2 LB/hr (di)cyclopentadiene (mostly CPD) and 14.1 LB./hr of toluene (a diluent) were fed into a Diels-Alder reactor and reacted in order to produce VNB. The reactor was operated at a temperature of 154° C. (310° F.) and at a pressure of 300 psi (2,067 kPa) to keep all reactants in the liquid phase. The residence time of the reactor was one hour, which resulted in a 33% conversion of the (di)cyclopentadiene.

The effluent from the Diels-Alder reactor was fed to a distillation column. The effluent contained BD, CPD, toluene, VCH, VNB, THI, DCPD, and trimers of BD/CPD.

The distillation column was maintained at an operating pressure of 12 psia (83 kPa). The temperature in the bottom of the column was maintained at about 175° C. (347° F.). The column had an internal diameter of 6 inches, and contained 60 feet of woven wire mesh packing.

The lighter boiling BD and CPD, along with the toluene, was removed as overhead and recycled to the Diels-Alder reactor via a heat exchanger and recycling line. The VNB was removed as a side-stream, along, with the VCH and with a small amount of CPD, THI, DCPD, and heavy by-products.

The remaining bottoms contained primarily THI, DCPD, and trimers and other oligimers of CPD, BD, and acyclics, most of which contained fourteen carbon atoms and were comprised of two CPD monomers and one BD monomer. The bottoms were exposed to the foregoing column conditions for 2 hours during which time approximately 90% of the DCPD in the bottoms cracked to monomeric CPD. The resulting CPD was removed as overhead and recycled to produce additional VNB.

The resulting DCPD-depleted heavy product was removed as a bottoms steam.

The presence of fouling in the heat exchanger providing heat for both the distillation and the cracking of DCPD to CPD was determined by calculating the heat transfer coefficient:

$$\frac{\text{Heat transfer coefficient}}{\text{Btu/hr ft}^2 \text{ °F.}} = \frac{(\text{Heat exchanged, Btu/hour})}{(\text{exchanger surface area ft}^2) \times (\text{steam temp} - \text{process temp, °F.})}$$

Figure 3:
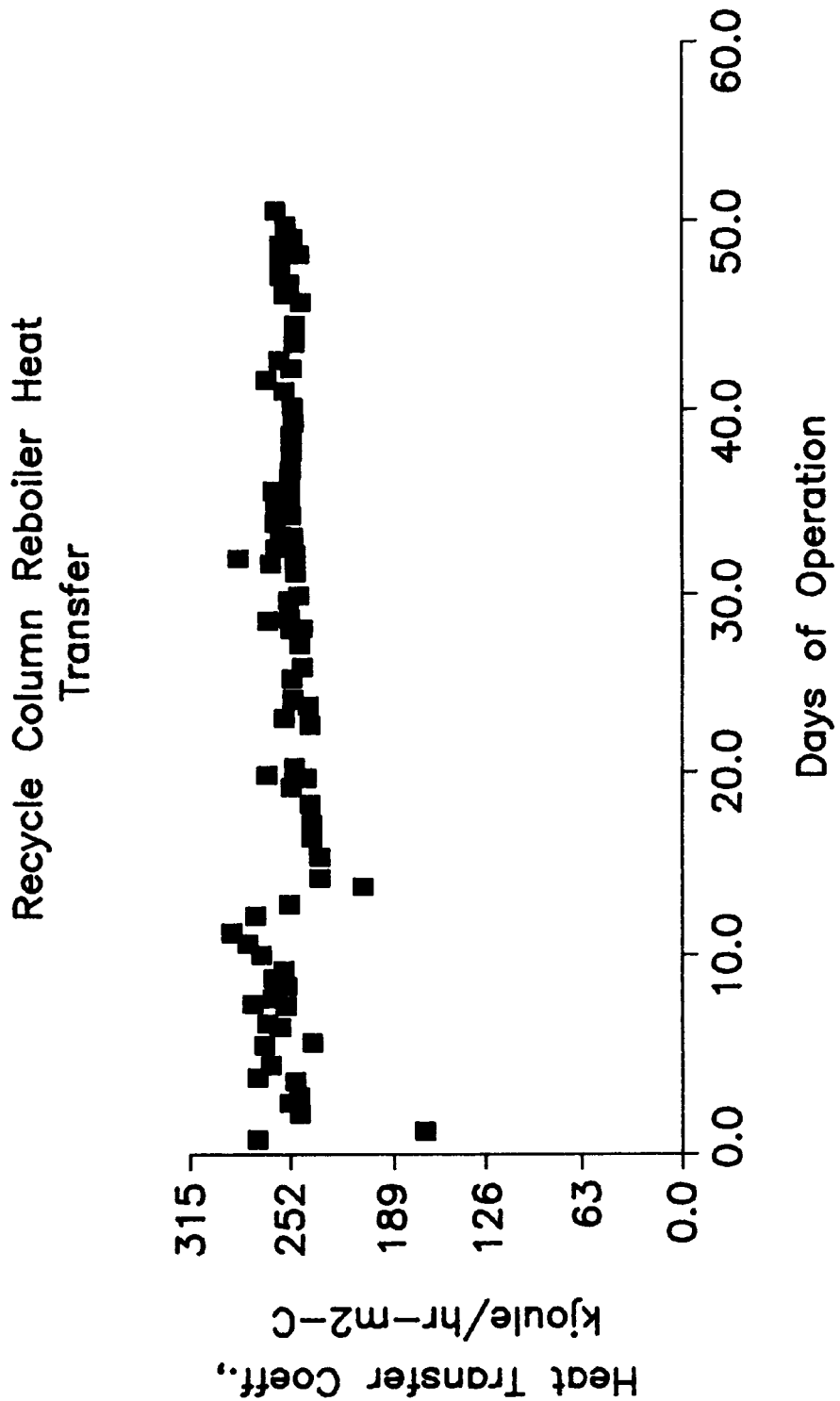
FIG. 3 is a graph of heat transfer coefficient of the heat exchanger used in Example I.

This data is plotted in the FIG. 3, and shows no decline in heat transfer coefficient over the duration of the run. This is an indication that fouling is not a problem.

Visual inspection of the reboiler following the total period of the run showed only a very thin film of polymer on the heat transfer surfaces. No polymer collected on the filters in the bottoms product effluent line.

EXAMPLE II

According to the embodiment of the invention described above in association with FIG. 4, an experiment was carried out in a continuously operating pilot plant for a period of two weeks. The Diels-Alder reaction was between ethylene and cyclopentadiene to produce norbornene (NB).

The pilot plant flow scheme was the same as that of FIG. 4. The Diels-Alder reactor was a 5 gallon continuous stirred-tank reactor. The reactor was equipped with a hot-oil jacket for temperature control and an internal magnetically driven stirrer for agitation. The reaction was operated at 800 psig pressure by controlling the back pressure of the reactor with a back pressure regulator.

The ethylene feed was introduced through a sparger in the bottom of the reactor via a mass flow meter. The liquid feeds were fed separately to the reactor from a feed drum and were controlled by a mass flow meter. The steady-state liquid feeds comprised of make-up DCPD, recycle CPD, hexane and Exxon Aromatic 200®.

The Diels-Alder reactor effluent was all liquid, as determined by flash computation at reactor effluent conditions. The reactor effluent was flashed at 40 psig into a separator drum. The bulk of unreacted ethylene was removed as a vapor from the separator drum. The liquid was sent to a recycle distillation column which was operated at a pressure of 15 psia. CPD and hexane were distilled off overhead, and recycled back to the Diels-Alder reactor via the same liquid feed drum.

A crude norbornene product was removed through a sidestream drawoff in the recycle distillation column at a point above the liquid feed line. The crude norbornene was sent to a second distillation column for further purification. TCD, DCPD, Aromatic 200®, and other heavy byproducts were distilled to the bottom of the second distillation column. The bottoms of the recycle distillation column were heated to a temperature of 235° C. The conversion of the heavy byproduct TCD to NB and CPD was from about 53% and to about 64%. The overall conversion of DCPD to CPD was from about 89% to about 93%.

The results obtained under four different conditions and different reactant ratios are shown below:

|  | A | B | C | D |
|---|---|---|---|---|
| CPD/$C_2^=$ molar ratio | 1.45 | 1.29 | 1.34 | 1.31 |
| $C_2^=$ Conversion in Diels-Alder reactor(%) | 80.4 | 76.0 | 74.6 | 68.8 |
| R-1 Temperature (° C.) | 210 | 210 | 210 | 199 |
| T-1 Bottoms Temperature (° C.) | 238 | 238 | 238 | 238 |
| T-1 Bottoms Residence Time (hr) | 2.8 | 2.7 | 2.9 | 3.7 |
| Norbornene Yield w/o operating 90 (LB./hr) | 0.211 | 0.226 | 0.219 | 0.201 |
| Norbornene Yield with operating 90 (LB./hr) | 0.236 | 0.249 | 0.239 | 0.216 |
| Yield Improvement (%) | 11.8 | 10.0 | 9.1 | 7.7 |

The results above show that substantial yield improvements of norbornene were achieved by using the present invention.

Persons of ordinary skill in the art will recognize that many modifications may be made to the present invention without departing from the spirit and scope of the present invention. The embodiment described herein is meant to be illustrative only and should not be taken as limiting the invention, which is defined solely in the following claims.

What is claimed is:

1. A method for producing alkenyl bridged ring compounds comprising:
   subjecting a feed comprising a mono-olefin and a cyclic diolefin to first conditions effective to produce a mixture comprising an alkenyl bridged ring product;
   subjecting said mixture to second conditions effective to separate said mixture into a light fraction and a heavy fraction wherein said heavy fraction comprises a major portion of said alkenyl bridged ring product;
   feeding said heavy fraction to a distillation column at a feed point;
   removing said alkenyl bridged ring product from said distillation column at a location above said feed point;
   heating a bottom portion of said distillation column under third conditions effective to decompose a part of heavy byproducts to form a recovered fraction comprising at least one compound selected from the group consisting of said mono-olefin, said cyclic diolefin, said alkenyl bridged ring product, and mixtures thereof; and
   separating said recovered fraction from said heavy byproducts.

2. The method of claim 1 wherein said mono-olefin is selected from the group consisting of ethylene, propylene, butene-1, cis-butene-2, trans-butene-2, isobutylene, cyclopentene, vinyl chloride, vinyl acetate, allyl acetate, styrene, and mixtures thereof.

3. The method of claim 1 wherein said cyclic diolefin is selected from the group consisting of cyclopentadiene, dicyclopentadiene, methylcyclopentadiene, 1,3-hexadiene, dimethylcyclopentadiene, cyclopentadiene-methylcyclopentadiene co-dimer, and mixtures thereof.

4. The method of claim 1 wherein said mono-olefin comprises ethylene.

5. The method of claim 1 wherein said cyclic diolefin comprises cyclopentadiene.

6. The method of claim 1 wherein said mono-olefin comprises ethylene and said cyclic diolefin comprises cyclopentadiene.

7. The method of claim 1 wherein said feed further comprises a light solvent.

8. The method of claim 1 wherein said feed further comprises a heavy solvent.

9. The method of claim 1 wherein said feed further comprises a light solvent and a heavy solvent.

10. The method of claim 7 wherein said light solvent comprises hexane.

11. The method of claim 9 wherein said feed further comprises hexane and a heavy solvent having a boiling point in the range of from about 190° C. to about 400° C.

12. The method of claim 1 wherein said alkenyl bridged ring product comprises norbornene.

13. The method of claim 1 wherein said recovered fraction is recycled to become part of said feed.

14. The method of claim 1 further including the step of separating said alkenyl bridged ring product in said recovered fraction.

15. The method of claim 1 further comprising recycling unreacted cyclic diolefin.

16. The method of claim 1 further comprising recycling unreacted mono-olefin.

17. The method of claim 1 wherein said mixture is produced in the presence of a catalyst.

* * * * *